US00PP25277P3

(12) United States Plant Patent
Couturieux

(10) Patent No.: US PP25,277 P3
(45) Date of Patent: Feb. 3, 2015

(54) ***CORYDALIS* PLANT NAMED 'COURIBLUE'**

(50) Latin Name: *Corydalis flexuosa×elata*
Varietal Denomination: COURIBLUE

(71) Applicant: Jacques Couturieux, Moyenmoutier (FR)

(72) Inventor: Jacques Couturieux, Moyenmoutier (FR)

( * ) Notice: Subject to any disclaimer, the term of this patent is extended or adjusted under 35 U.S.C. 154(b) by 124 days.

(21) Appl. No.: 13/815,528

(22) Filed: Mar. 7, 2013

(65) Prior Publication Data

US 2014/0259240 P1 Sep. 11, 2014

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

*Primary Examiner* — Annette Para
(74) *Attorney, Agent, or Firm* — Cassandra Bright

(57) ABSTRACT

A distinct new cultivar of *Corydalis* plant named 'COURIBLUE', characterized by an exceptionally long flowering season, flowering continuously from approximately mid Spring until first frost in the Fall. Plants are upright, vigorous, free flowering and perennial. The new cultivar is a *Corydalis* typically suited for ornamental container and landscape use.

1 Drawing Sheet

Latin name of the genus and species: *Corydalis flexuosa× elata.*

Variety denomination: 'COURIBLUE'.

BACKGROUND OF THE INVENTION

The new *Corydalis* is the result of a planned breeding program conducted by the inventor, Jacques Couturieux at a commercial nursery in Lorraine, France. The seed parent is an unnamed, unpatented variety of *Corydalis flexuosa* and the pollen parent is an unnamed, unpatented variety of *Corydalis elata.*

The variety was selected after the inventor noted the continuous flower characteristics. After 2 seasons of observation, the inventor confirmed a vigorous plant habit and exceptionally long flowering season of *Corydalis* 'COURIBLUE'.

Asexual reproduction by tissue was first performed in a non-commercial laboratory during 2009. Plants produced have proved to be stable and reproduced true to type in successive generations.

SUMMARY OF THE INVENTION

The cultivar 'COURIBLUE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'COURIBLUE'. These characteristics in combination distinguish 'COURIBLUE' as a new and distinct *Corydalis* cultivar:

1. Exceptionally long flowering season, typically in France from the end of April until October, when the first frosts occur.
2. Continuous flowering.
3. Vigorous, perennial garden performance.
4. Sweet honey like scent.
5. Unique blue flower coloration.
6. Good tolerance for cold temperatures.

PARENTAL COMPARISON

Plants of the new cultivar 'COURIBLUE' are similar to the seed parent, *Corydalis flexuosa* in most horticultural characteristics. However, plants of 'COURIBLUE' differ in that they are more vigorous, and more floriferous. Additionally, the flowering season for 'COURIBLUE' is longer, and flowering occurs continuously during the season, whereas plants of *Corydalis flexuosa* flower sporadically.

Plants of the new cultivar 'COURIBLUE' are similar to the pollen parent, known *Corydalis flexuosa* in some horticultural characteristics. However, plants of 'COURIBLUE' differ in that they are shorter, and more floriferous. Additionally, the new variety produces flowers earlier in the Spring, and flowers longer into the Fall months.

COMMERCIAL COMPARISON

Plants of the new cultivar 'COURIBLUE' are similar to the known commercial variety, *Corydalis flexuosa* 'Blue Panda', unpatented in some horticultural characteristics. However, plants of 'COURIBLUE' differ in that they are taller, more vigorous, and more floriferous. Additionally, the new variety begins producing at least 2 weeks earlier in the Spring, and flowers longer into the Fall than 'Blue Panda'.

BRIEF DESCRIPTION OF THE PHOTOGRAPH

The accompanying photograph in FIG. 1 illustrates in full color a typical plants of 'COURIBLUE' grown outdoors in a garden in Lorraine, France. This plant is approximately 15 months old. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'COURIBLUE' plants grown outdoors in Lorraine, France at a commercial nursery. The growing temperature ranged from 0° C. to 12° C. at night to 8° C. to 22° C. during the day. During the winter period December to March, plants were sheltered in a large poly-tunnel with day temperatures ranging from 5° C. to 18° C., and night temperatures ranging from −5° C. to +8° C. No artificial light, photoperiodic treatments or chemical treatments were given to the plants. Measurements and numerical values represent averages of typical flowering types.

Botanical classification: *Corydalis flexuosa×elata* 'COURIBLUE'.

Age of the plant described: Approximately 15 months.

Container size of the plant described: 2 liter commercial container.

PROPAGATION

Time to produce a flowering plant from rooted plantlet: Nine to twelve months.

Root description: Densely fibrous.

Rooting habit: Freely branching.

PLANT

Plant and growth habit: Vigorous, upright, mounding perennial. Plant height: 40 to 50 cm to top of flowering plane. Approximately 20 to 30 cm to top of foliar plane.

Plant diameter: Approximately 35 cm.

Lateral stems:

*Quantity*.—Average 20.

*Diameter*.—Average 0.7 cm.

*Length*.—Average 18 cm.

*Texture*.—Glabrous.

*Strength*.—Moderately strong, very flexible.

*Color*.—Near RHS Green 143C, flushed Greyed-Red 181C.

FOLIAGE

Arrangement: Compound ternate.

Length of blade: 4 to 5 cm.

Width of blade: 5 to 6 cm.

Shape of blade: Broadly ovate.

Leaflets: Individual leaflets are sessile and, palmately 3-lobed, approximately 0.5 cm to 1 cm deep from apex.

*Shape*.—Deltoid.

*Length*.—3.5 to 4 cm.

*Diameter*.—2.5 to 3.5 cm.

Apex: Obtuse.

Base: Cordate.

Margin: Entire.

Texture, upper surface: Glabrous, matte.

Texture, lower surface: Glabrous, matte.

Venation pattern: Palmate.

Color:

*Developing foliage, upper surface*.—Near RHS Green 141B.

*Developing foliage, lower surface*.—Near RHS Green 141C.

*Fully expanded foliage, upper surface*.—Near RHS Green 143A. Venation: Near RHS Yellow-Green 144B. Fully expanded foliage, lower surface: Near RHS Green 137C. Venation: Near RHS Yellow-Green 144B.

Petiole:

*Length*.—Approximately 10 cm cm.

*Diameter*.—About 1.5 mm.

*Texture, upper and lower surfaces*.—Glabrous.

*Color, upper and lower surfaces*.—Close to Yellow-Green N144A.

FLOWER

Flower arrangement and habit: Racemes of approximately 20 tubular, zygomorphic flowers. Flowers have an extended lower lip, composed of 3 fully fused petals, a slightly shorter up lip composed of 2 fully fused petals, all fused at the base into a spur-like structure.

Natural flowering season: From late April to October, or first frost outdoors in scentral France. Individual flowers last about 8 to 14 days on the plant.

Inflorescence height: Approximately 15 to 20 cm.

Inflorescence diameter: Approximately 9 cm.

Flower diameter: Approximately 2 cm.

Flower length: Approximately 2.5 cm.

Flower bud:

*Shape*.—Tubular.

*Length*.—1.5 to 2 cm.

*Diameter*.—0.8 to 1.0 cm.

*Color*.—Near RHS Blue 105D.

Flower color: Petals are fused, coloration is consistent throughout flower, including spur.

*Color*.—When opening, exterior surface: Near RHS Blue 105D. When opening, interior surface: Near RHS Blue 106A. Fully opened, exterior surface: Near RHS Blue 107A. Fully opened, interior surface: Near RHS Blue 107B. Aging, exterior surface: Near RHS Blue 100A. Aging, interior surface: Near RHS Blue 100B.

Petals:

*Apex*.—Upper lip acute, lower lip obtuse.

*Base*.—Fused.

*Texture*.—Upper surface: Glabrous, silky matte.

*Texture*.—Lower surface: Glabrous, silky matte.

Sepals: Not Present.

Peduncles:

*Length*.—Average 10 cm.

*Diameter*.—Approximately 0.4 cm.

*Aspect*.—Erect or slight outward angle.

*Texture*.—Glabrous.

*Color*.—Near RHS Greyed-Red 181B.

Pedicels:

*Length*.—Average 2.0 cm.

*Diameter*.—0.3 cm.

*Aspect*.—Average about 45 degrees from vertical.

*Texture*.—Glabrous.

*Color*.—Near Yellow-Green 146B to C, tinged Greyed-Red 181B.

Fragrance: Sweet, moderately strong.

REPRODUCTIVE ORGANS

Androecium:

*Stamen number per flower*.—2, each with 3 anthers. Highly reduced, approximately 0.2 cm.

*Pollen*.—Not observed.

Gynoecium:

*Pistil number per flower*.—1.

*Pistil length*.—About 1.3 m.

*Style color*.—Close to Yellow-Green 149D.
*Ovary color*.—Close to Yellow-Green 144B.

OTHER CHARACTERISTICS

Seed/fruit: Not observed to date.
Environmental tolerance: Plants of the new *Corydalis* have good garden performance in rich, organic soil and are hardy to USDA zone 6.
Diseases and pests: Neither resistance nor susceptibility to normal diseases and pests of *Corydalis* has been observed.

What is claimed is:

1. A new and distinct cultivar of *Corydalis flexuosa×elata* plant named 'COURIBLUE' as herein illustrated and described.

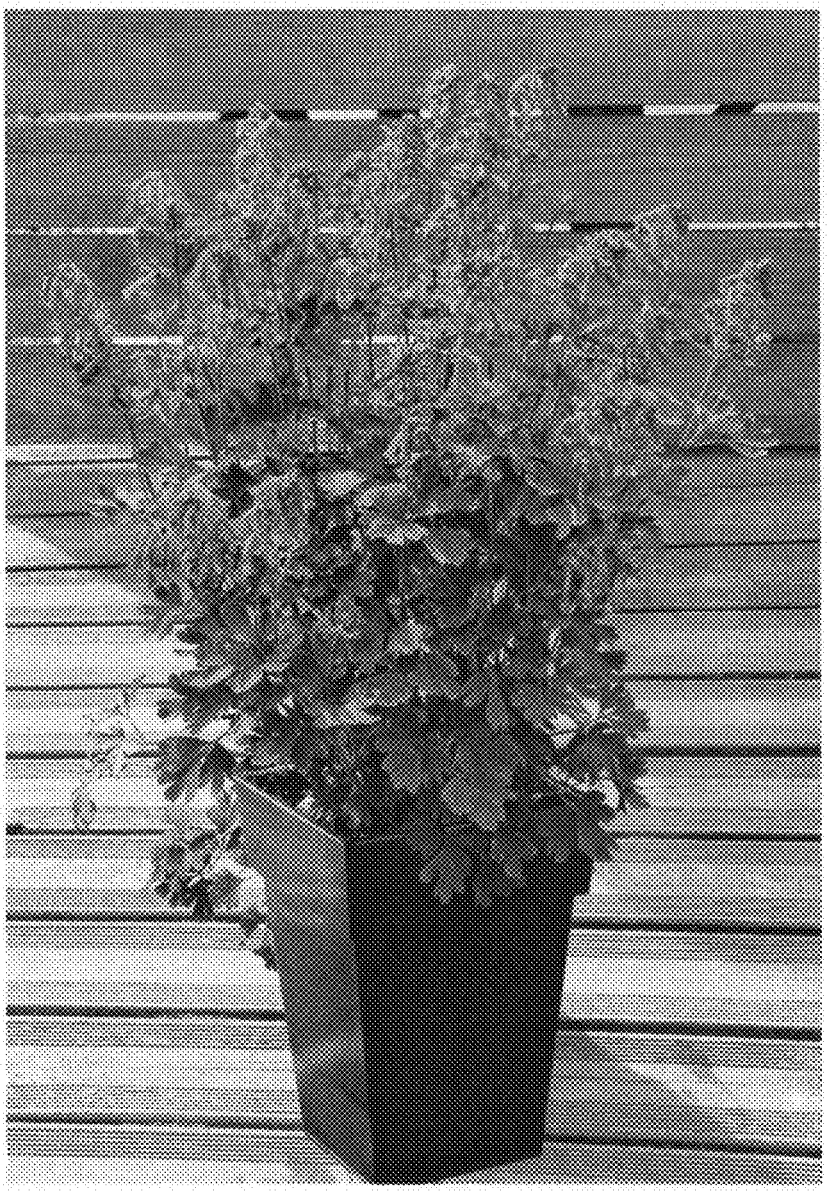

* * * * *